(12) United States Patent
Meyer-Lückel et al.

(10) Patent No.: US 8,686,063 B2
(45) Date of Patent: *Apr. 1, 2014

(54) METHOD OF INFILTRATING ENAMEL LESIONS

(75) Inventors: Hendrik Meyer-Lückel, Berlin (DE); Sebastian Paris, Neuruppin (DE); Andrej M. Kielbassa, Berlin (DE)

(73) Assignee: Charité—Universitätsmedizin Berlin, Berlin (DE)

( * ) Notice: Subject to any disclaimer, the term of this patent is extended or adjusted under 35 U.S.C. 154(b) by 961 days.

This patent is subject to a terminal disclaimer.

(21) Appl. No.: 11/432,271

(22) Filed: May 11, 2006

(65) Prior Publication Data

US 2006/0264532 A1  Nov. 23, 2006

Related U.S. Application Data

(63) Continuation-in-part of application No. 11/040,442, filed on Jan. 21, 2005, now Pat. No. 7,485,673.

(51) Int. Cl.
*A61L 24/06* (2006.01)
*A61K 6/02* (2006.01)
*A61K 6/08* (2006.01)
*A61K 6/083* (2006.01)

(52) U.S. Cl.
USPC ........... 523/115; 523/113; 523/116; 523/118; 433/226; 433/228.1

(58) Field of Classification Search
USPC .................. 523/115, 113, 116, 118; 423/481; 424/78.08; 433/216, 217.1, 226, 228.1
See application file for complete search history.

(56) References Cited

U.S. PATENT DOCUMENTS

| 4,515,910 | A  | * | 5/1985 | Rawls et al. ................. 523/115 |
| 6,326,417 | B1 |   | 12/2001 | Jia |
| 6,482,871 | B1 |   | 11/2002 | Aasen et al. |
| 6,753,001 | B2 |   | 6/2004 | Jia et al. |
| 2003/0134934 | A1 | * | 7/2003 | Kojima et al. ............... 523/120 |
| 2003/0157034 | A1 |   | 8/2003 | Jia et al. |

(Continued)

FOREIGN PATENT DOCUMENTS

| FR | 2 542 198 A1 | 9/1984 |
| WO | WO 00/74587 | 12/2000 |

OTHER PUBLICATIONS

Davila, J.M. et al. "Adhesive penetration in human artificial and natural white spots" *J Dent Res*, 1975, 54:999-1008.

(Continued)

*Primary Examiner* — Michael Pepitone
(74) *Attorney, Agent, or Firm* — Saliwanchik, Lloyd & Eisenschenk

(57) ABSTRACT

The present invention refers to a method of infiltrating enamel for the prevention and/or treatment of carious lesions comprising (a) exposing an enamel area to a conditioner comprising hydrochloric acid; (b) exposing the conditioned enamel area to an infiltrant; and (c) curing the infiltrant. The present invention further refers to a kit for carrying out the method of infiltrating enamel, which comprises a conditioner comprising hydrochloric acid and an infiltrant comprising at least one low viscous dental resin. The present invention also refers to a method for identifying an infiltrant by calculation of the penetration coefficient, and to an infiltrant identified by the method having a penetration coefficient of >50 cm/s or comprising a low viscous light curing resin having a penetration coefficient of >50 cm/s.

5 Claims, 11 Drawing Sheets

(56) References Cited

U.S. PATENT DOCUMENTS

| | | | |
|---|---|---|---|
| 2003/0162864 A1* | 8/2003 | Pearson et al. | 523/115 |
| 2003/0175218 A1 | 9/2003 | Kanca, III | |
| 2004/0229973 A1* | 11/2004 | Sang et al. | 523/118 |
| 2006/0167129 A1 | 7/2006 | Meyer-Luckel et al. | |

OTHER PUBLICATIONS

De Araujo, F.B. et al. "Diagnosis of approximal caries: Radiographic versus clinical examination using tooth separation" *Am J Dent*, 1992, 5:245-248.

Ekstrand, K.R. and Martignon, S. "Managing approximal carious lesions: A new non-operative approach" *Caries Res*, 2004, 38:361, abstract No. 12.

García-Godoy, F. et al. "Caries progression of white spot lesions sealed with an unfilled resin" *J Clin Pediatr Dent*, 1997, 21:141-143.

Goepferd, S.J. and Olberding, P. "The effect of sealing white spot lesions on lesion progression in vitro" *Pediatric Dent.*, 1998, 11:14-16.

Gray, G.B. and Shellis, P. "Infiltration of resin into white spot caries-like lesions of enamel: An in vitro study" *Eur J Prosthodont Restor Dent*, 2002, 10:27-32.

Hamid, A. and Hume, W.R. "Diffusion of resin monomers through human carious death in vitro" *Endod Dent Traumatol*, 1997, 13:1-5.

Kogon, S.L. e t al. "Can radiographic criteria be used to distinguish between cavitated and noncavitated approximal enamel caries?" *Dentomaillofac Radiol*, 1987, 16:33-36.

Larsen, M.J. and Fejerskov, O. "Surface etching and subsurface demineralization of dental enamel induced by a strong acid" *Scand. J. Dent. Res.*, 1977, 85:320-326.

Marthaler, T.M. and Germann, M. "Radiographic and visual appearance of small smooth surface caries lesions studied on extracted teeth" *Caries Res*, 1970, 4:224-242.

Mejàre, I. et al. "Caries development from 11 to 22 years of age: A prospective radiographic study" *Caries Res*, 1998, 32:10-16.

Meyer-Lueckel, H. et al. "Influence of the application time on the penetration of different dental adhesives and a fissure sealant into artificial subsurface lesions in bovine enamel" *Dent Mat*, 2006, 22:22-28.

Meyer-Lueckel, H et al. "The penetration of various adhesives into initial enamel lesions in vitro" *Schweiz Monatsschr Zahnmed*, 2005, 155:316-323, summary—p. 323.

Ratledge, D.K. et al. "A clinical and microbiological study of approximal carious lesions" *Caries Res*, 2001, 35:3-7.

Robinson, C. et al. "In vitro studies of the penetration of adhesive resins into artificial caries-like lesions" *Caries Res*, 2001, 35:136-141.

Robinson, .C et al. "Arrest and control of carious lesions: A study based on preliminary experiments with resorcinol-formaldehyde resin" *J Dent Res*, 1976, 55:812-818.

Rugg-Gunn, A.J. "Approximal carious lesions—A comparison of the radiological and clinical appearances" *Br Dent J*, 1972, 133:481-484.

Schmidlin, P.R. et al. "Sealing smooth enamel surfaces with a newly devised adhesive patch: a radiochemical in vitro analysis" *Dent Mater*, 2005, 21:545-550.

Schmidlin, P.R. at al. "Penetration of a bonding agent into De- and remineralized enamel in vitro" *J Adhes Dent*, 2004, 6:111-115.

Spurr, A.R. "A low-viscosity epoxy resin embedding medium for electron microscopy" *J Ultrastruct Res*, 1969, 26:31-43.

Paris, S. "Sealing of initial enamel lesions with various adhesives and a fissure sealant at different penetration times in vitro" Doctoral thesis at Fachbereich Humanmedizin, Freie Universität Berlin, 2005, translation of pp. 55-56.

Seeman, R. et al. "Caries Preventative Potential of an Adhesive Patch for Proximal Sealing: A Microbial-Based in vitro Study" *Caries Research*, 52nd ORCA Congress, 2005, 39:321, meeting abstract No. 101.

Mueller, J. et al. "Inhibition of Lesion Progression by the Penetration of Resins In Vitro: Influence of the Application Procedure" *Operative Dentistry*, 2006, 31-33:338-345.

Paris. S. et al. "Progression of Sealed Initial Bovine Enamel Lesions under Demineralizing Conditions in vitro" *Caries Research*, 2006, 40:124-129.

Wikepedia article: "Human tooth", From Wikipedia, the free encyclopedia, http://en.wikipedia.org/wiki/Human_tooth, Apr. 24, 2013.

* cited by examiner

METHOD OF INFILTRATING ENAMEL LESIONS

CROSS-REFERENCE TO RELATED APPLICATION

The present application is a continuation-in-part of U.S. application Ser. No. 11/040,442, filed Jan. 21, 2005, now U.S. Pat. No. 7,485,673, which is hereby incorporated by reference herein in its entirety, including any figures, tables, nucleic acid sequences, amino acid sequences, and drawings.

BACKGROUND OF THE INVENTION

In industrial countries, about 98% of the adult population exhibits one or more carious lesions or are already provided with fillings. Any carious lesion which eventually may lead to cavitation is initiated by demineralization of the hard tooth substance. At an early stage, referred to as "initial enamel caries", the tooth surface remains intact without visible signs of erosion but the demineralized area below the surface becomes more and more porous.

Today, the only non-operative ways to treat approximal caries are to enhance remineralization by application of fluorides and to arrest lesion progress by improvement of patient's oral hygiene. While smooth surfaces of the tooth are more susceptible for improved cleaning strategies, approximal surfaces are particularly difficult to clean. Nevertheless, remineralization in approximal lesions that have reached the dentin seems to be hardly achievable, since several clinical studies showed that from this threshold a visible cavitation of the lesion is established in most cases (Rugg-Gunn A J. Approximal carious lesions. A comparison of the radiological and clinical appearances. *Br Dent J*, 1972, 133:481-484; De Araujo F B et al. Diagnosis of approximal caries: radiographic versus clinical examination using tooth separation. *Am J Dent*, 1992, 5:245-248; Ratledge et al. A clinical and microbiological study of approximal carious lesions. Part 1: The relationship between cavitation, radiographic lesion depth, the site-specific gingival index and the level of infection of the dentine. *Caries Res*, 2001, 35:3-7). Moreover, in vitro studies even found many cavitations in lesions confined to enamel. A cavitated enamel lesion cannot be cleaned sufficiently by the patient and will progress (Marthaler T M and Germann M. Radiographic and visual appearance of small smooth surface caries lesions studied on extracted teeth. *Caries Res*, 1970, 4:224-242; Kogon S L et al. Can radiographic criteria be used to distinguish between cavitated and noncavitated approximal enamel caries? *Dentomaillofac Radiol*, 1987, 16:33-36). Therefore, if a cavitation occurs even at such an early stage of the caries process, a remineralization seems very unlikely under clinical conditions. This could explain clinical findings, that fluoridation and improved oral hygiene can only slow down the progression of approximal caries but are not capable of reversing it (Mejare I et al. Caries development from 11 to 22 years of age: A prospective radiographic study. Prevalence and distribution. *Caries Res*, 1998, 32:10-16).

Once a cavitation has developed, invasive methods of treatment are generally indicated. However, drilling out carious tooth material is always accompanied by the removal of non-carious, i.e. sound, hard tooth substance. In approximal carious lesions which are difficult to reach, the ratio of carious and intact substance being removed is particularly unfavorable. Moreover, the connection between an inserted filling and the endogenous tooth material is susceptible for carious lesions itself, and renewal of fillings due to the ageing process leads to further removal of sound tooth material. Therefore, methods of treating caries at an early stage, and in particular approximal initial carious lesions, are highly desirable in order to prevent later requirement for invasive procedures.

One apparent indication of initial enamel caries are white spot lesions. Such a lesion is characterized by a loss of mineral in the bulk of enamel, whereas the surface of the lesion remains relatively intact (so-called "pseudo-intact surface layer"). A promising approach of non-operative dentistry might be the sealing of enamel lesions with low viscous light curing resins such as dental adhesives and fissure sealants. The tiny pores within the lesion body act as diffusion pathways for acids and dissolved minerals and, therefore, enable the dissolution of enamel at the advancing front of the lesion. The aim of the proposed regimen is not only to seal the surface but to infiltrate these pores, thereby withdrawing the lesion body from further attack. Moreover, after curing the resin material, a mechanical support of the fragile enamel framework in the lesion will be achieved. Therefore, an occlusion of the pores by infiltration with light curing resins might arrest the lesion progression and mechanically stabilize the fragile lesion structure.

The idea to arrest caries by sealing with low viscous resins has been followed in several in vitro experiments since the seventies of the last century (Robinson C et al. Arrest and control of carious lesions: A study based on preliminary experiments with resorcinol-formaldehyde resin. *J Dent Res*, 1976, 55:812-818; Davila J M et al. Adhesive penetration in human artificial and natural white spots. *J Dent Res*, 1975, 54:999-1008; Gray G B and Shellis P. Infiltration of resin into white spot caries-like lesions of enamel: An in vitro study. *Eur J Prosthodont Restor Dent*, 2002, 10:27-32; Garcia-Godoy F et al. Caries progression of white spot lesions sealed with an unfilled resin. *J Clin Pediatr Dent*, 1997, 21:141-143; Robinson C et al. In vitro studies of the penetration of adhesive resins into artificial caries-like lesions. *Caries Res*, 2001, 35:136-141; Schmidlin P R et al. Penetration of a bonding agent into de- and remineralized enamel in vitro. *J Adhes Dent*, 2004, 6:111-115). It could be shown that sealants can penetrate the body of artificial lesions nearly completely (Gray G B and Shellis P. Infiltration of resin into white spot caries-like lesions of enamel: An in vitro study. *Eur J Prosthodont Restor Dent*, 2002, 10:27-32; Meyer-Lueckel, H et al. Influence of the application time on the penetration of different adhesives and a fissure sealant into artificial subsurface lesions in bovine enamel. *Dent Mater* 2006, 22:22-28), and reduce the accessible pore volumes within the lesions significantly (Robinson C et al. In vitro studies of the penetration of adhesive resins into artificial caries-like lesions. *Caries Res*, 2001, 35:136-141). Moreover, it has been observed that sealants are capable to inhibit further lesion progress under demineralizing conditions (Robinson C et al. Arrest and control of carious lesions: A study based on preliminary experiments with resorcinol-formaldehyde resin. *J Dent Res*, 1976, 55:812-818; García-Godoy F et al. Caries progression of whit spot lesions sealed with an unfilled resin. *J Clin Pediatr Dent*, 1997, 21:141-143; Robinson et al. In vitro studies of the penetration of adhesive resins into artificial caries-like lesions. *Caries Res*, 2001, 35:136-141; Muller J et al. Inhibition of lesion progression by penetration of resins in vitro: Influence of the application procedure. *Oper Dent*, in press; Paris S et al. Progression of sealed initial bovine enamel lesions under demineralizing conditions in vitro. *Caries Res*, 2006, 40:124-129).

However, one of the problems in sealing natural enamel lesions is that "pseudo-intact surface layers" have higher mineral contents compared to carious bodies of lesion. As a consequence, these layers inhibit the penetration of the lesion body by the sealing material and may even function as a barrier. In the end, the surface layer may be superficially sealed, but the carious body may be insufficiently penetrated by the resin. At worst, the carious process further proceeds below the "seal".

Efforts have been made to enhance the penetration of sealants in enamel lesions. In an in vitro model, artificial enamel lesions were produced showing an intact surface layer, a body of lesion and a progressive demineralization front. It has been shown that a 5 seconds etching of those artificially induced lesions with phosphoric acid resulted in deeper penetration depths (Gray G B and Shellis P. Infiltration of resin into white spot caries-like lesions of enamel: An in vitro study. *Eur Prosthodont Restor Dent,* 2002, 10:27-32). Thus, such a pretreatment or "conditioning" of an enamel area by etching could also improve the penetration of sealant in vivo. However, artificially induced enamel lesions differ from natural lesions in that they comprise regular and relatively thin "pseudo-intact surface layers". Natural enamel lesions, in contrast, usually show higher mineralized surface layers of varying thickness. Thus, conditioning with phosphoric acid, although demonstrated as successful in vitro, must not necessarily provide for a benefit in vivo.

WO 00/09030 discloses a teeth-coating method that protects teeth from caries and peridontal diseases along with giving color to them. This coating method consists of the steps of (a) etching the teeth, for example by acid or laser; (b) application of a protective substance to the etched teeth; and (c) sealing the teeth. For acid etching, commonly employed materials such as phosphoric acid, maleic acid, citric acid and pyruvic acid are mentioned.

Nevertheless, an in vivo study reported that the application of a conventional adhesive onto enamel lesions pre-treated with phosphoric acid gel resulted in retardation of caries progression compared to controls (Ekstrand et al. *Caries Res,* 2004, 38:361). However, patients were monitored for two years only and diagnosis was done by X-raying, a rather insensitive method for analyzing successful penetration. Therefore, the results of this study should be regarded with some caution, as even the authors concede. Moreover, it remains unclear whether this initial success would be seen after longer periods since the rather superficial "seal" might be destroyed due to the physical load in vivo.

In the previous studies only commercially available adhesives and fissure sealants which have been optimized for adhesive purposes have been used to penetrate subsurface enamel lesions. Composite resins optimized to rapidly infiltrate these enamel lesions ("infiltrants") might achieve better sealing results. In order to develop such composite resins, a better understanding of the processes occurring during the penetration of enamel lesions is needed.

Physically, the penetration of a liquid (uncured resin) into a porous solid (enamel lesion) is described by the Washburn equation (Equation 1, see below). This equation assumes that the porous solid is a bundle of open capillaries (Buckton G. Interfacial phenomena in drug delivery and targeting. Chur, 1995); in this case, the penetration of the liquid is driven by capillary forces.

$$d^2 = \left(\frac{\gamma \cdot \cos\theta}{2\eta}\right) r \cdot t \qquad \text{-Equation 1-}$$

d distance, moved by the liquid resin
γ surface tension of the liquid resin (to air)
θ contact angle of the liquid resin (to enamel)
η dynamic viscosity of the liquid resin
r capillary (pore) radius
t penetration time The bracketed term of the Washburn equation is the penetration coefficient (PC, Equation 2, see below) (Fan P L et al. Penetrativity of sealants. *J Dent Res,* 1975, 54:262-264). The PC is composed of the liquid's surface tension to air (γ), the cosine of the liquid's contact angle to enamel (θ) and the dynamic viscosity of the liquid (η). The higher the coefficient is, the faster the liquid penetrates a given capillary or porous bed. This means that a high PC can be achieved for high surface tensions, low viscosities and low contact angles where the influence of the contact angle is comparatively low.

$$PC = \left(\frac{\gamma \cdot \cos\theta}{2\eta}\right) \qquad \text{-Equation 2-}$$

PC penetration coefficient
γ surface tension of the liquid resin (to air)
θ contact angle of the liquid resin (to enamel)
η dynamic viscosity of the liquid resin Previously, a positive correlation between the penetration coefficients (PCs) of commercial sealants and their ability to penetrate into fissures could be found (O'Brien W J et al. Penetrativity of sealants and glazes. The effectiveness of a sealant depends on its ability to penetrate into fissures. *Oper Dent,* 1987, 3:51-56). Moreover, low viscous sealants showed deeper penetration when applied on etched enamel (Irinoda Y et al. Effect of sealant viscosity on the penetration of resin into etched human enamel. *Oper Dent* 2000, 25:274-282). However, no study has hitherto focused on the influence of the PC on resin penetration into carious lesions. The penetration of five commercially available adhesives and one fissure sealant into artificial enamel lesions was subject of a recent study (Meyer-Lueckel, H et al. Influence of the application time on the penetration of different adhesives and a fissure sealant into artificial subsurface lesions in bovine enamel. *Dent Mater,* 2006, 22:22-28). The penetration depth was shown to depend on penetration time. In this study, the best performing commercially available material Excite® penetrated 105 μm in 30 seconds and completely filled artificial enamel lesions. The square correlation between penetrated depth and time arising from the Washburn equation (see Equation 1) showed that enormous penetration times are needed if a deep infiltration of natural lesion (>1000 μm) is aimed with commercially available materials. This underlines the need for faster penetration composites. However, application times of more than 120 seconds are hardly acceptable for use in a dentist's daily practice due to economical reasons.

Thus, there is still a strong need for improved non-operative procedures of treating initial or even advanced enamel lesions in order to inhibit caries progression.

It is therefore an object of the present invention to provide for methods and means enabling improved resin penetration of initial or advanced enamel lesions.

BRIEF SUMMARY OF THE INVENTION

The present invention refers to a method of infiltrating enamel, in particular for the prevention and/or treatment of carious lesions. The present invention further refers to a kit for carrying out said method of infiltrating enamel, which comprises a conditioner comprising hydrochloric acid and an infiltrant comprising at least one low viscous dental resin. The present invention also refers to a method for identifying an infiltrant by calculation of the penetration coefficient, and to infiltrants or low viscous dental resins having a penetration coefficient of >50 cm/s.

DETAILED DESCRIPTION OF THE INVENTION

Figure 1:
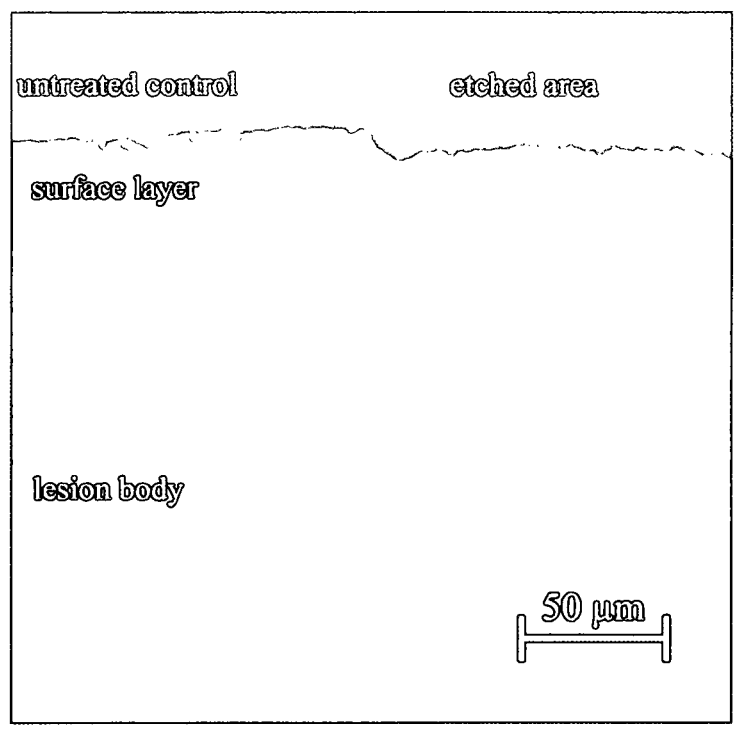
FIG. 1 shows an initial enamel carious lesion after conditioning with 37% of phosphoric acid gel for 30 seconds (results obtained by the Confocal Laser Scanning Microscope, CLSM, imaging technique).

The object of the present invention is solved by a method of infiltrating enamel, comprising the following steps:
 (a) exposing an enamel area to be infiltrated to a conditioner comprising hydrochloric acid;
 (b) exposing the enamel area conditioned in step (a) to an infiltrant; and
 (c) curing the infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl)triclodecane; BEMA, benzyl methacrylate; SIMA, 3-trimethoxysilane propyl-methacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl)benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

The object of the present invention is further solved by a use of a method of infiltrating enamel according to the present invention for the prevention and/or treatment of a carious lesion in a subject in need thereof.

In one embodiment, the subject is a mammal, preferably a human.

The object of the present invention is also solved by a kit for infiltrating enamel, comprising at least the following:
 (a) a conditioner comprising hydrochloric acid; and
 (b) an infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In a further embodiment, the conditioner further comprises additives selected from the group comprising glycerol, highly dispersed silicon dioxide and methylene blue.

In one embodiment, the infiltrant comprises at least one low viscous resin.

In a preferred embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl)triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a particularly preferred embodiment, the low viscous resin is selected from the group comprising polymethacrylic acid and derivatives thereof.

In a most preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl)benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

The object of the present invention is also solved by a use of a kit for infiltrating enamel for the prevention and/or treatment of a caries lesion in a subject in need thereof.

In one embodiment, the subject is a mammal, preferably a human.

The object of the present invention is also solved by a method for preparing the kit.

The object of the present invention is also solved by the use of hydrochloric acid for the manufacture of a medical product for the prevention and/or treatment of a carious lesion.

In one embodiment, the medical product is based on a gel comprising about 1-30% (w/w) of hydrochloric acid.

In a preferred embodiment, the medical product is based on a gel comprising about 5-15% (w/w) of hydrochloric acid.

In a further embodiment, the medical product further comprises additives selected from the group comprising glycerol, highly dispersed silicon dioxide and methylene blue.

The object of the present invention is also solved by a method for manufacturing the medical product.

The object of the present invention is also solved by an infiltrant comprising at least one low viscous resin.

In one embodiment, the low viscous resin is selected from the group comprising bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-pentanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl)triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

In a preferred embodiment, the low viscous resin is selected from the group comprising polymethacrylic acid and derivatives thereof.

In a particularly preferred embodiment, the low viscous resin is selected form the group comprising bis-GMA, 2,2-bis[4-(2-hydroxy-3-methacryloxypropoxy)phenyl]propane; UDMA, 1,6-bis(methacryloxy-2-ethoxycarbonylamino)-2,4,4-trimethylhexan; TEGDMA, triethylene glycol dimethacrylate; and HEMA, 2-hydroxyethyl methacrylate.

In a further embodiment, the infiltrant further comprises additives selected from the group comprising CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl)benzotriazol; TIN326, Tinuvin 326; TIN350, Tinuvin 350; Tin328, Tinuvin 328; HQME, hydroxyquinone monomethyl ester; BHT 2,6-di-t-butyl-4-methyl phenol; MBP 2,2-methylene-bis(6-t-butylphenol); MBEP, 2,2-Methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

The object of the present invention is further solved by a method for preparing an infiltrant.

The object of the present invention is also solved by the use of an infiltrant, preferably an infiltrant according to the present invention, for the manufacture of a medical product for the prevention and/or treatment of a carious lesion.

The object of the present invention is also solved by a method for manufacturing the medical product.

The object of the present invention is further solved by a method for identifying an infiltrant having a penetration coefficient of >50 cm/s or an infiltrant comprising a low viscous light curing resin having a penetration coefficient of >50 cm/s using the following equation:

$$PC = \left(\frac{\gamma \cdot \cos\theta}{2\eta}\right) \qquad \text{-Equation 2-}$$

wherein:
PC refers to the penetration coefficient;
γ refers to the surface tension of the liquid resin (to air);
θ refers to the contact angle of the liquid resin (to enamel); and
η refers to the dynamic viscosity of the liquid resin.

The object of the present invention is further solved by an infiltrant identified using the method for identifying an infiltrant having a penetration coefficient of >50 cm/s or an infiltrant comprising a low viscous light curing resin having a penetration coefficient of >50 cm/s using the equation as given above (Equation 2).

The object of the present invention is further solved by an infiltrant having a penetration coefficient of >50 cm/s or comprising a low viscous light curing resin having a penetration coefficient of >50 cm/s.

In a preferred embodiment, the penetration coefficient of >50 cm/s is determined using Equation 2 above.

In a particularly preferred embodiment, the low viscous resin comprises 22% bis-GMA, 2,2-bis[4-(2-hydroxy-3-methacryloxypropoxy)phenyl]propane; 67% TEGDMA, triethylene glycol dimethacrylate; 10% ethanol; >1% DABE, ethyl 4-(dimethylamino)benzoate, and >1% camphorquinone.

The object of the present invention is further solved by a method for the prevention and/or treatment of a carious lesion using an infiltrant according to the present invention.

The object of the present invention is further solved by a use of an infiltrant according to the present invention for the manufacture of a medical product for the prevention and/or treatment of a carious lesion.

The object of the present invention is further solved by a method of infiltrating enamel for the prevention and/or treatment of a carious lesion in a subject in need thereof comprising the following steps:

(a) exposing an enamel area to be infiltrated to a conditioner comprising hydrochloric acid;
(b) exposing the enamel area conditioned in step (a) to an infiltrant having a penetration coefficient of >50 cm/s or to an infiltrant comprising a low viscous light curing resin having a penetration coefficient of >50 cm/s; and
(c) curing the infiltrant.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In one embodiment, the subject is a mammal, preferably a human.

The object of the present invention is further solved by a kit for infiltrating enamel, comprising:

(a) a conditioner comprising hydrochloric acid; and
(b) an infiltrant having a penetration coefficient of >50 cm/s or an infiltrant comprising a low viscous light curing resin having a penetration coefficient of >50 cm/s.

In one embodiment, the conditioner is based on a gel comprising about 1-30% (w/w) of hydrochloric acid.

In a preferred embodiment, the conditioner is based on a gel comprising about 5-15% (w/w) of hydrochloric acid.

In one embodiment, the kit further comprises a device for application of the hydrochloric acid and/or the infiltrant.

The term "exposing" as used herein refers to any procedure by which the enamel is provided with the conditioner or the infiltrant. Mostly, an exposure will be achieved by simple application, e.g., by spreading. For that purpose, the kit may additionally comprise one or more devices suitable for supporting the application, e.g., a brush, a sponge, a tissue, a pipette, a syringe or such.

It is considered by the present invention that the conditioner may be removed prior to application of the infiltrant. Thus, the kit may additionally comprise any device for that purpose.

It is further considered by the present invention that surplus infiltrant may be removed. Thus, the kit may additionally comprise any device for that purpose.

Preferably, the conditioner is allowed to remain applied for about 60-300 seconds, more preferably, the conditioner is allowed to remain applied for about 90-120 seconds.

Preferably, the infiltrant is allowed to remain applied for up to about 120 seconds, more preferably, the infiltrant is allowed to remain applied for about 120 seconds.

Most preferably, the infiltrant has a penetration coefficient of >50 cm/s and is remained applied for less than 60 seconds.

Preferably, the infiltrant is applied twice.

An "enamel area to be infiltrated" preferably is an area comprising a carious lesion. However, in order to prevent such lesions, i.e. for prophylaxis, any carious damage may be also absent in this area.

The conditioner may alternatively be based on an aqueous solution or may also be embedded in a plaster.

It is also considered by the present invention that the conditioner may additionally comprise phosphoric acid up to about 40% (w/w), preferably in the range of about 20% to 37% (w/w).

"Curing of the infiltrant" is preferably achieved by light-induced polymerization.

To enable access to the approximal surface, a separation of the carious teeth could be performed using orthodontic elastics. This technique is well documented for diagnostic purposes.

The resins according to the present invention are further considered for use as dental adhesives and/or fissure sealants.

Said resins cited above may be used, e.g., within the infiltrant of the present invention, either separately or in any combination thereof.

The term "penetration coefficient" of an infiltrant refers to the ability of a liquid (infiltrant) to rapidly penetrate into a porous solid (caries lesion). It is composed of the following physical properties: surface tension to air (γ), contact angle to the solid (θ) and dynamic viscosity (η) (see Equation 2).

The "surface tension γ" of an infiltrant (to air) refers to the force acting on a liquid-gas interface resulting in thin film on the surface. It is caused by an increased attraction of molecules at the surface of a liquid resulting from forces of attraction on fewer sides of the molecules.

The term "contact angle θ" of an infiltrant (to enamel) refers to the tangent angle at the interface between the droplet of a liquid (infiltrant) and a solid surface (enamel).

The term "dynamic viscosity η" of an infiltrant refers to a measure of the resistance to flow of a fluid under an applied force. Dynamic viscosity is the tangential force per unit area (shear or tangential stress) required to move one horizontal plane with respect to the other at unit velocity when maintained a unit distance apart by the fluid (velocity gradient or rate of shear).

In conclusion, the present invention provides for an improved penetration of enamel lesions, e.g., initial or advanced enamel lesions, by an infiltrant. Within the prior art, methods of sealing enamel are available which, however, bear the risk of only superficially sealing the "pseudo-intact surface layer" but leaving the body of lesion insufficiently penetrated by the resin. Using the methods and means, e.g., the conditioner and/or the infiltrants or the low viscous resins, according to the present invention, occlusion of the body of lesion becomes possible.

First, by exposing an enamel area to be infiltrated to the conditioner comprising hydrochloric acid, the "pseudo-intact surface layer" is removed such that infiltration of carious areas by the infiltrant is greatly facilitated. Second, the resins cited above exhibit very low viscosity properties, and thus the infiltrant readily reaches the pores of the lesion to occlude them.

Furthermore, the present invention provides a method for determining the penetration coefficient (PC) of an infiltrant, allowing the identification and thus a preparation of an infiltrant having good penetrating properties while simultaneously exhibiting acceptable application times. On the basis of PCs determined according to said method, improved infiltrants, e.g., composites, can be developed.

By using the methods and means according to the present invention, invasive treatment of an enamel lesion may be prevented or at least delayed. Due to the non-operative character of the sealing procedure, the patient's compliance will be greatly enhanced. The method is well practicable with low costs. Finally, the inventive method may represent a therapeutic link between pure prophylaxis and invasive treatment of caries.

EXAMPLES

Example 1

Effect of the Pre-Treatment with a Conditioner Comprising Hydrochloric Acid

1. Material and methods
1.1 Sample Preparation

Extracted human molars and premolars, showing approximal white spots were cut across the demineralizations. One-hundred-twenty lesions confined to the outer enamel were selected. The cut surface as well as half of each lesion, thus serving as control, was covered with nail varnish. Subsequently, the lesions were etched with either phosphoric (37%) or hydrochloric (5% or 15%) acid gel for 30 to 120 seconds (n=10).
1.2 Visualization The specimens were dried for 5 minutes in a silicone hose, closed at one end with a stopper, and separated with silicone rings. Subsequently, Spurr's resin (Spurr A R. A low-viscosity epoxy resin embedding medium for electron microscopy. *J Ultrastruct Res*, 1969, 26:31-43), labeled with 0.1 mmol/l of the fluorescent dye Rhodamine B Isothiocyanate (RITC), was doused over the specimens and the hose was closed with another stopper. The resin was cured in an autoclave (Ivomat IP3; Ivoclar Vivadent, Schaan, Liechtenstein) at 0.8 MPa and 70° C. for 8 hours. Under this pressure, the very low viscous resin penetrated into the remaining pores of the lesion. After curing, the specimens were cut, fixed on object holders, parallelized and polished up to 4000 grit (Exakt Mikroschleifsystem; Exakt Apparatebau). This infiltration technique was termed VIsualisation by Resin INfiltration (VIRIN).
1.3 CLSM Imaging The specimens were studied using a Confocal Laser Scanning Microscope (CLSM) (Leica TCS NT; Leica, Heidelberg, Germany). The excitation light was generated with an Ar/Kr-Laser and had a maximum wavelength at 560 nm. The images were recorded in fluorescent mode. The emitted light was conducted through a 590 nm long pass filter to make sure that only fluorescent light was detected and reflected light was suppressed. Specimens were observed with a 40× objective using oil immersion. The observed layer was approximately 10 µm below the surface. Laser beam intensity and photo multiplier amplification were kept constant during the investigation. The images (250×250 µm) were taken with a resolution of 1024×1024 pixels and 256 pseudo color steps (red/black) and analyzed using the ImageJ Program (NIH; Rockville Pike, Md., USA).
2. Results The thickness of the surface layers in the control and the etched parts as well as the erosions in the sound and diseased tissues were measured. Etching with $H_3PO_4$ gel for 30 seconds did not alter the thickness of the surface layer significantly (p>0.05; t-test). However, the surface layer reduction was significantly increased in lesions etched with 15% HCl gel for 90 seconds compared to those etched with $H_3PO_4$ gel for 30 or 90 seconds (p<0.05; ANOVA). No significant differences in the depths of erosion in the lesions compared to sound enamel could be observed (p>0.05; t-test).

Figure 2:
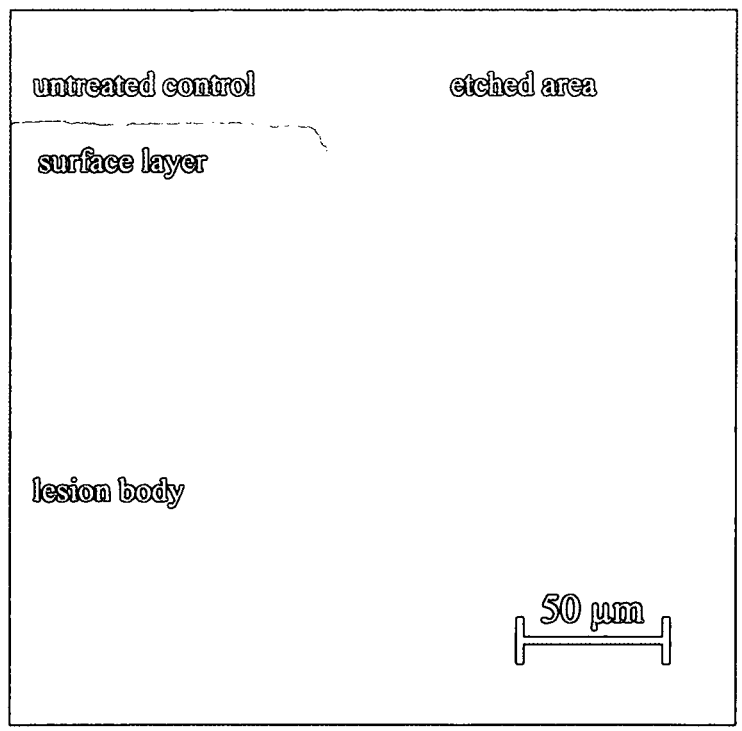
FIG. 2 shows an initial enamel carious lesion after conditioning with 15% hydrochloric acid gel for 120 seconds (results obtained by CLSM).

In FIG. 1, it is shown that pre-treatment of initial enamel carious lesions with 37% of phosphoric acid gel for 30 seconds resulted in only insufficient etching of the "pseudo-intact surface layer". Thus, this kind of pre-treatment is not capable of destabilizing the surface layer to an extent necessary for optimal penetration of the infiltrant. In consequence, sealing will be only superficial. Incomplete infiltration, however, does not protect from organic acids and dissolution of enamel and erosion will further proceed. In FIG. 2, it is shown that pre-treatment with 15% of hydrochloric acid gel for 120 seconds resulted in complete removal of the "pseudo-intact surface layer".

It can be concluded that a reliable reduction of the surface layer can be achieved by etching with 15% hydrochloric acid gel for 90 to 120 seconds.

Example 2

Resin Infiltration of Natural Caries Lesions after Etching with Phosphoric and Hydrochloric Acid Gels In Vitro 1. Material and Methods Extracted human molars and premolars showing proximal white spot lesions were used in this study. After careful cleaning from soft tissues teeth were stored in 20% ethanol solution up to usage. Teeth were examined using a 20× stereo microscope (Stemi SV 11; Carl Zeiss, Oberkochen, Germany) and cavitated as well as damaged lesions were excluded.

For radiographic examination teeth were positioned in a silicone base with the buccal aspect facing to the radiographic tube (Heliodent M D; Siemens, Bensheim, Germany). To simulate cheek scatter a 15 mm wall of clear Perspex was placed between the tube and the teeth. Standardized radiographs (0.12 seconds, 60 kV, 7.5 mA) were taken from each tooth (Ektaspeed; Kodak, Stuttgart, Germany) and developed using an automatic processor (XR 24-II; Dürr Dental, Bietigheim-Bissingen, Germany). The radiographic lesion depths were assessed by two examiners independently and scored (Marthaler T M and Germann M. Radiographic and visual appearance of small smooth surface caries lesions studied on extracted teeth. *Caries Res*, 1970, 224-242): no translucency (R0), translucency confined to the outer half on enamel (R1), translucency to the inner half of enamel (R2), translucency to the outer half of dentin (R3) and to the inner half of dentin (R4). In case of disagreement in assessment of radiographic lesion depth a consensus rank was concerted.

The roots of the teeth were removed and the crowns were cut across the carious lesions perpendicular to the surface (Band Saw; Exakt Apparatebau, Norderstedt, Germany) providing two halves of each lesion. Subsequently, the cut surfaces were examined (stereo microscope) and classified with respect to the histological lesion extension (C1-C3). Lesions extending into the inner half of dentin (C4) were excluded. Corresponding lesion halves showing equal caries extension were assigned to the treatment (TRT) group (n=10 each). When corresponding lesion halves differed in extension, only the deeper one was used as control (CTR; n=10).

Subsequently, the cut surfaces were covered with nail varnish. In the TRT groups corresponding lesion halves were either etched with 37% phosphoric acid gel ($H_3PO_4$; total etch; Ivoclar Vivadent, Schaan, Liechtenstein) or with an experimental 15% hydrochloric acid gel (HCl). The HCl gel contained hydrochloric acid 15%, glycerol 19%, highly dispersed silicon dioxide 8% and methylene blue 0.01% in aqueous solution. After 120 seconds the gels were rinsed thoroughly with water spray for 30 seconds. In the CTR group no acid etching was performed. Lesions were immersed with pure ethanol for 30 seconds and subsequently dried for 60 seconds using oil free compressed air.

A dental adhesive (Excite; Ivoclar Vivadent) labeled with 0.1% tetramethylrhodamine isothiocyanate (TRITC; Sigma Aldrich, Steinheim, Germany) was applied onto the lesion surfaces. The resin was allowed to penetrate into the lesions for 5 minutes. Subsequently, excessive material was removed and the resin was light cured for 30 seconds (Translux CL; Heraeus Kulzer, Hanau, Germany) at 400 mW/cm$^2$. The nail varnish was carefully removed, and specimen halves were fixed on object holders parallel to the cut surface and polished (Exakt Mikroschleifsystem, Abrasive Paper 2400, 4000; Exakt Apparatebau, Norderstedt, Germany). In order to stain remaining pores, the specimens were immersed in 50% ethanol solution containing 100 µM/l sodium fluorescein (Sigma Aldrich) for 3 hours.

Specimens were observed using a confocal laser scanning microscope (CLSM Leica TCS NT; Leica, Heidelberg, Germany) in double fluorescence mode using a 10× objective. The excitation light had two wavelength maxima at 488 and 568 nm. The emitted light was split by a 580 nm reflection short pass filter and paned through a 525/50 nm band pass filter for FITC and a 590 nm long pass filter for RITC detection. Images with a lateral dimension of 1000×1000 µm$^2$ and a resolution of 1024×1024 pixels were recorded and analyzed using AxioVision LE software (Zeiss, Oberkochen, Germany). Penetration depths and thickness of the (residual) surface layer for the lesion halves were measured at up to 10 defined points (depending on the lesion size; indicated by a 100 µm grit) and mean values were calculated.

Statistical analysis was performed using SPSS software (SPSS for Windows 11.5.1; SPSS Inc., Chicago, Ill., USA). Data were checked for normal distribution using the Kolgomorov Smirnov test. To analyze differences between lesion halves/acid gels Wilcoxon test for paired samples was used. For comparison between unpaired groups Mann-Whitney tests and Kruskal-Wallis tests were performed.

Figure 3A:
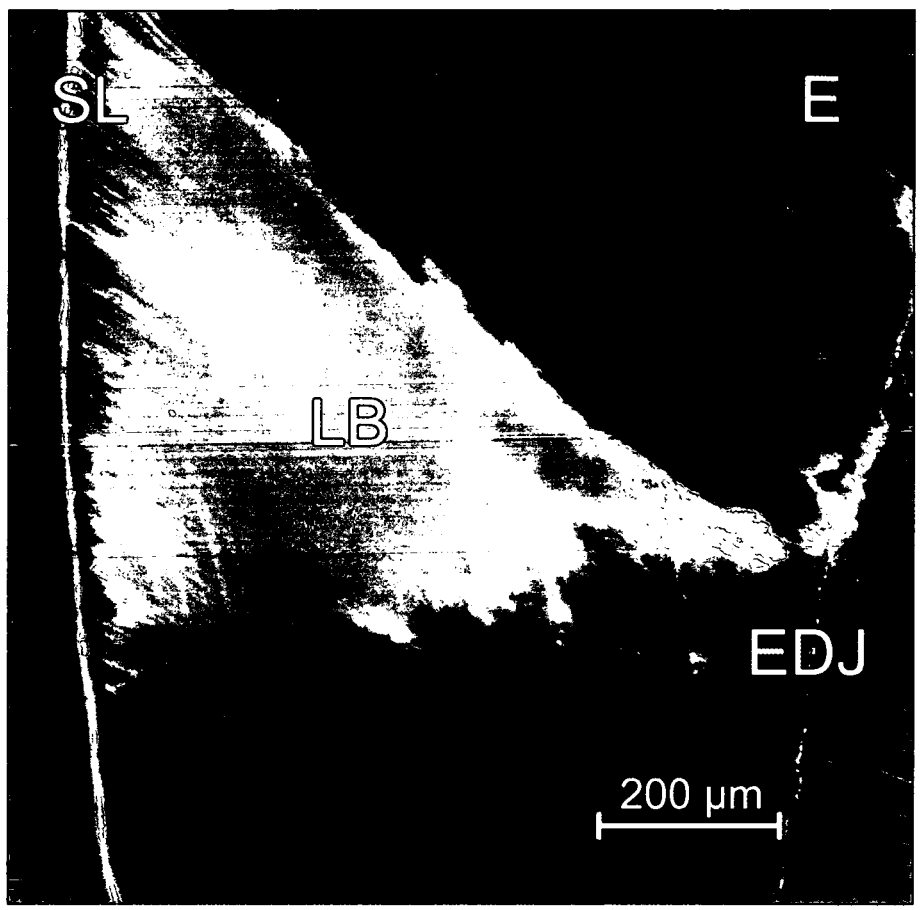
FIGS. 3A-3C show representative confocal microscopic images of resin infiltrated lesions (E: sound enamel; SL: surface layer; LB: lesion body; R: penetrated resin; EDJ: enamel-dentin junction; S: lesion surface); A: The surface layer of this $H_3PO_4$-etched caries lesion was not eroded completely. Therefore, only superficial resin penetration occurred (indicated by a fine rim of red fluorescence at the tooth surface); B: Deep resin penetration is observed in this HCl-etched lesion without visible surface layer remnants; C: Magnified image of an HCl-etched lesion (40× objective). The outermost 50-100 µm of prism cores are filled with resin. In non-infiltrated parts of the lesion body the highly porous prism centers show green fluorescence.
Figure 3B:
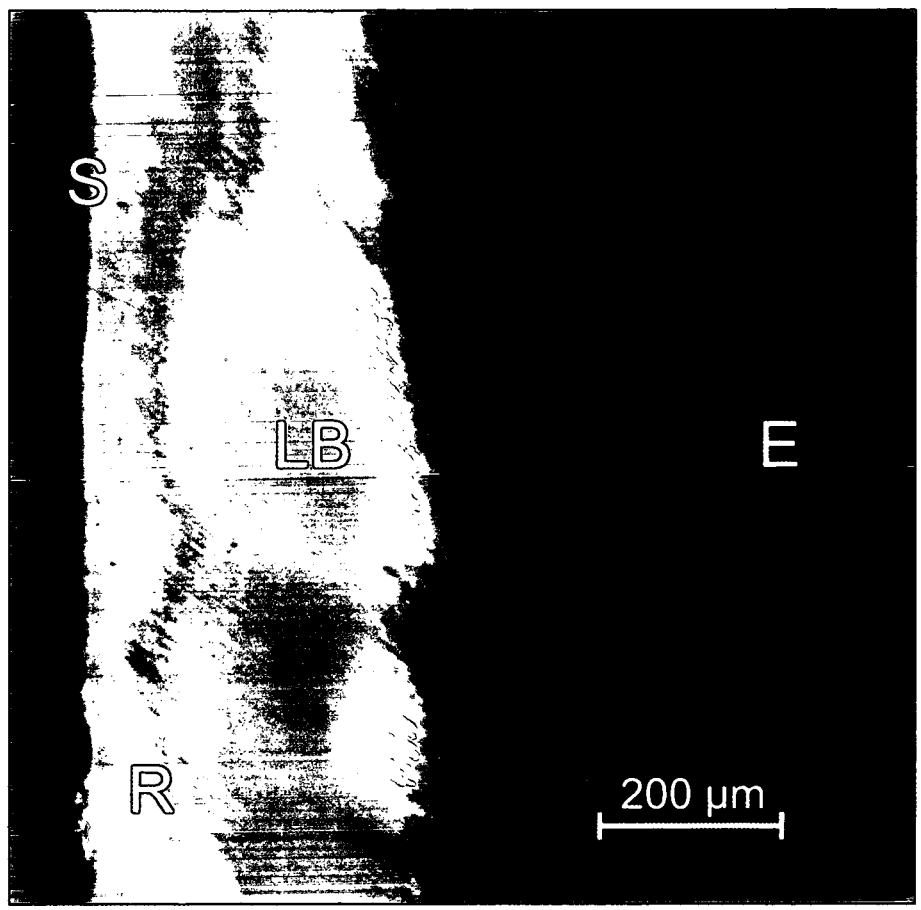
Figure 3C:
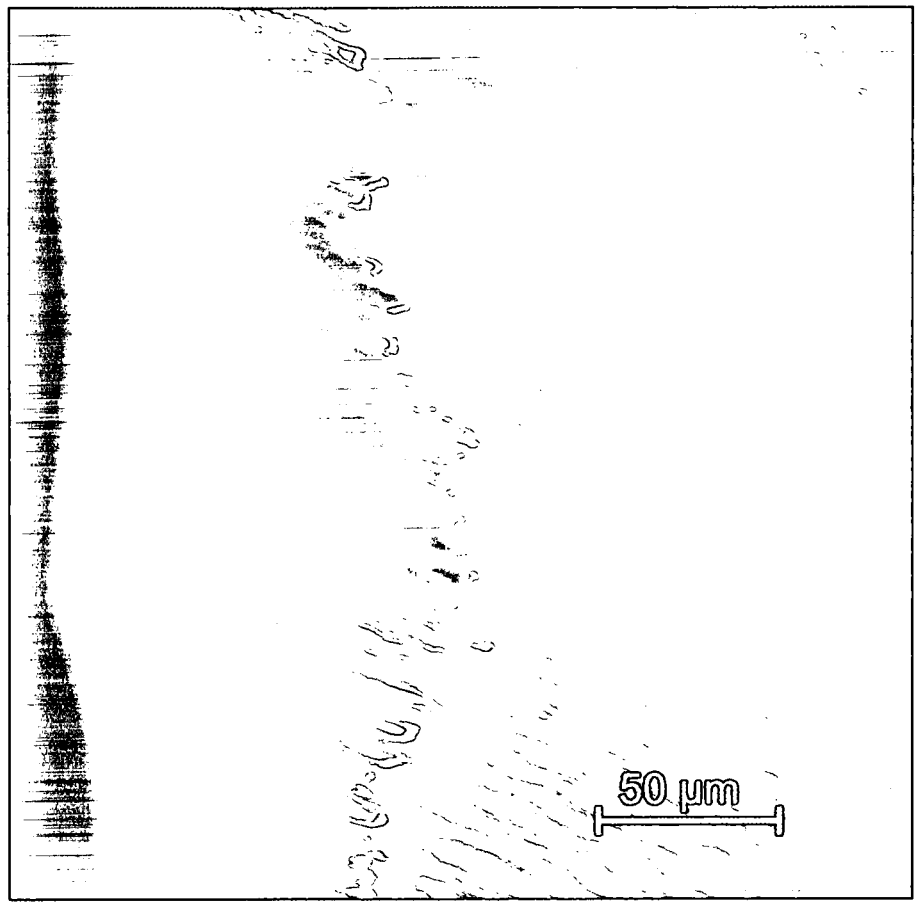

2. Results:

In the CLSM images, the penetrated resin showed a red fluorescence, whereas remaining pores within the lesion as well as dentin appeared green (FIG. 3A-C). Solid material as sound enamel or the surface layer was displayed black.

Figure 4:
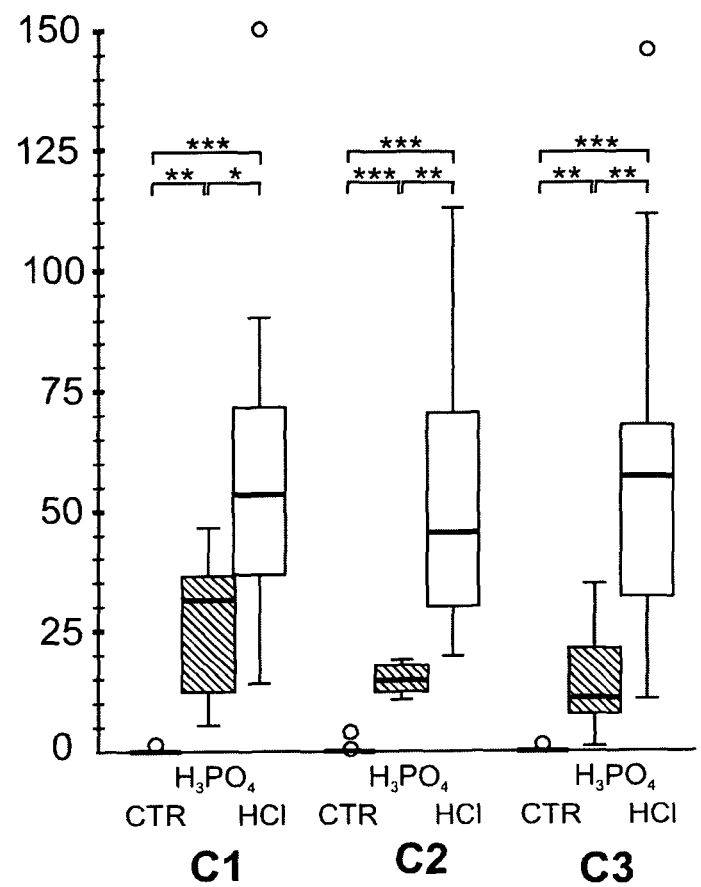
FIG. 4 shows mean penetration depths (y-axis) for various lesion extensions (box and whisker plots with quartiles and medians). Statistically significant differences between groups are indicated with asterisks (* $p<0.05$;  $p<0.01$; * $p<0.01$; Wilcoxon/Mann-Whitney).

Penetration depths varied considerably. FIG. 4 shows the penetration depths of the various groups for different caries extensions. For lesion halves etched with HCl gel the mean penetration depth (standard deviation) [58 (37) µm] was significantly higher compared with those of lesions treated with $H_3PO_4$ gel [18 (11) µm] (p<0.001; Wilcoxon). Without acid etching no resin penetration was found [0 (1) µm]. Within treatment groups no significant differences for penetration depths could be observed between various lesion extensions (C1-C3) (p>0.05; Kruskal-Wallis). Similarly, penetration depths were comparable for radiographic lesion depths (R1-R3) (p>0.05; Table 1).

For those lesions where the surface layer was completely removed (CTR n=0; $H_3PO_4$ n=2; HCl n=8) significantly higher (p<0.01; Mann-Whitney) mean penetration depths [65 (35) µm] could be found compared to lesions, where residues of the surface layer remained after etching [33 (31) µm]. Surface layer thickness was significantly reduced after HCl etching [20 (18) µm] compared to lesions etched with phosphoric acid [37 (25) µm] and to the non-etched CTR group [42 (23) µm] (p>0.05; Mann-Whitney).

TABLE 1

Mean penetration depths [µm (standard deviations)] for the various radiological caries extensions.

| group | | radiolucency | | | |
|---|---|---|---|---|---|
| | | R0 | R1 | R2 | R3 |
| TRT | CTR | 0 (0)$_{n=8}$ | 0 (0)$_{n=10}$ | 1 (1)$_{n=8}$ | 0 (0)$_{n=4}$ |
| | $H_3PO_4$ | 25 (15)$_{n=6}$ | 17 (12)$_{n=10}$ | 16 (7)$_{n=8}$ | 16 (10)$_{n=6}$ |
| | HCl | 47 (27)$_{n=6}$ | 65 (41)$_{n=10}$ | 52 (27)$_{n=8}$ | 67 (52)$_{n=6}$ |

Example 3

Evaluation of the PCs of Experimental Infiltrants

The aim of this investigation was the evaluation of the PCs of 66 experimental composite resins intended to infiltrate enamel lesions (infiltrants).

1. Material and Methods

A total of 66 experimental infiltrants containing two of the monomers BisGMA, UDMA, TEGDMA and HEMA in variable weight proportions each (100:0; 75:25; 50:50; 25:75; 0:100) as well as ethanol (0%, 10% or 20%) were prepared (Table 2). For each experimental resin, 10 g were mixed up in brown glass jars according to Table 2. To avoid premature polymerization, the resins were stored at 4° C. until use. To determine PCs of the experimental infiltrants, contact angles, surface tensions, and viscosities were measured.

TABLE 2

Composition (weight percent) and measured results of experimental infiltrants.
Means and standard deviations (SD) are given for contact angles, surface tensions,
dynamic viscosities and resulting penetration coefficients (PCs). In addition, the
consistency after light curing is displayed.

| N° | BisGMA (%) | TEGDMA (%) | HEMA (%) | UDMA (%) | EtOH (%) | Contact Angle θ (°) | (cos) | Viscosity η (mPa s) | Surface Tension γ (mN/m) | PC (cm/s) | Consistency after curing |
|---|---|---|---|---|---|---|---|---|---|---|---|
| 1 | 100 | | | | | * | * | * | * | * | hard |
| 2 | 90 | | | | 10 | 54.2 (2.5) | 0.58 | 6637.0 (1.2) | 40.6 (0.1) | 0.2 | hard |
| 3 | 80 | | | | 20 | 47.8 (0.9) | 0.67 | 750.3 (2.3) | 34.7 (0.1) | 1.6 | hard |
| 4 | | 100 | | | | 7.0 (0.4) | 0.99 | 8.4 (0.0) | 34.7 (0.0) | 204.1 | hard |
| 5 | | 90 | | | 10 | 3.7 (0.1) | 1.00 | 5.8 (0.0) | 31.5 (0.0) | 273.1 | hard |
| 6 | | 80 | | | 20 | 3.2 (0.1) | 1.00 | 3.6 (0.0) | 28.0 (0.0) | 390.7 | hard |
| 7 | | | 100 | | | 11.0 (0.6) | 0.98 | 5.2 (0.0) | 34.6 (0.0) | 326.8 | hard |
| 8 | | | 90 | | 10 | 7.5 (0.5) | 0.99 | 4.0 (0.0) | 32.1 (0.0) | 393.8 | viscous |
| 9 | | | 80 | | 20 | 4.2 (0.4) | 1.00 | 3.2 (0.0) | 30.2 (0.0) | 474.9 | liquid |
| 10 | | | | 100 | | 44.9 (3.2) | 0.71 | * | * | * | hard |
| 11 | | | | 90 | 10 | 33.6 (0.6) | 0.83 | 412.0 (9.7) | 35.4 (0.0) | 3.6 | hard |
| 12 | | | | 80 | 20 | 32.5 (1.0) | 0.84 | 84.5 (0.0) | 33.3 (0.0) | 16.6 | hard |
| 13 | 75 | 25 | | | | 30.5 (1.2) | 0.86 | 3345.7 (4.0) | 38.4 (0.0) | 0.5 | hard |
| 14 | 67.5 | 22.5 | | | 10 | 23.8 (0.8) | 0.91 | 272.2 (0.3) | 35.5 (0.0) | 6.0 | hard |
| 15 | 60 | 20 | | | 20 | 17.0 (0.5) | 0.96 | 59.0 (0.0) | 30.1 (0.1) | 24.4 | hard |
| 16 | 50 | 50 | | | | 26.1 (2.9) | 0.90 | 186.4 (0.1) | 36.5 (0.0) | 8.8 | hard |
| 17 | 45 | 45 | | | 10 | 20.8 (1.6) | 0.93 | 31.4 (0.0) | 33.2 (0.0) | 49.4 | hard |
| 18 | 40 | 40 | | | 20 | 10.1 (0.1) | 0.98 | 16.4 (0.0) | 30.3 (0.0) | 91.1 | hard |
| 19 | 25 | 75 | | | | 16.9 (0.9) | 0.96 | 26.9 (0.0) | 35.5 (0.0) | 63.3 | hard |
| 20 | 22.5 | 67.5 | | | 10 | 5.1 (0.7) | 1.00 | 12.7 (0.0) | 33.0 (0.0) | 129.3 | hard |
| 21 | 20 | 60 | | | 20 | 5.0 (0.9) | 1.00 | 7.8 (0.0) | 29.1 (0.0) | 185.4 | hard |
| 22 | 75 | | 25 | | | 33.2 (1.2) | 0.84 | 2344.1 (2.4) | 38.3 (0.0) | 0.7 | hard |
| 23 | 67.5 | | 22.5 | | 10 | 29.7 (1.1) | 0.87 | 243.5 (0.2) | 34.9 (0.0) | 6.2 | hard |
| 24 | 60 | | 20 | | 20 | 28.6 (2.2) | 0.88 | 60.8 (0.2) | 30.5 (0.0) | 22.1 | hard |
| 25 | 50 | | 50 | | | 14.4 (0.2) | 0.97 | 52.4 (0.2) | 36.3 (0.0) | 33.6 | hard |
| 26 | 45 | | 45 | | 10 | 12.4 (0.8) | 0.98 | 37.2 (0.0) | 33.3 (0.0) | 43.6 | hard |
| 27 | 40 | | 40 | | 20 | 5.5 (0.8) | 1.00 | 17.7 (0.0) | 30.8 (0.0) | 86.7 | hard |
| 28 | 25 | | 75 | | | 14.4 (1.9) | 0.97 | 18.5 (0.0) | 35.4 (0.0) | 92.7 | hard |
| 29 | 22.5 | | 67.5 | | 10 | 8.9 (1.0) | 1.00 | 10.9 (0.0) | 32.5 (0.0) | 149.3 | hard |
| 30 | 20 | | 60 | | 20 | 5.1 (0.3) | 1.00 | 7.0 (0.0) | 30.4 (0.0) | 216.5 | rubbery |
| 31 | 75 | | | 25 | | 53.9 (2.2) | 0.59 | * | * | * | hard |
| 32 | 67.5 | | | 22.5 | 10 | 49.1 (3.0) | 0.65 | 1919.8 (26.4) | 38.7 (0.0) | 0.7 | hard |
| 33 | 60 | | | 20 | 20 | 44.7 (0.7) | 0.71 | 238.1 (0.2) | 30.8 (0.0) | 4.6 | hard |
| 34 | 50 | | | 50 | | 52.2 (3.4) | 0.61 | * | * | * | hard |
| 35 | 45 | | | 45 | 10 | 41.3 (1.0) | 0.75 | 1350.4 (2.4) | 36.9 (0.1) | 1.0 | hard |
| 36 | 40 | | | 40 | 20 | 38.9 (0.2) | 0.78 | 156.3 (0.2) | 30.6 (0.0) | 7.6 | hard |
| 37 | 25 | | | 75 | | 48.0 (3.0) | 0.67 | * | * | * | hard |
| 38 | 22.5 | | | 67.5 | 10 | 39.1 (1.3) | 0.78 | 737.3 (0.7) | 35.8 (0.0) | 1.9 | hard |
| 39 | 20 | | | 60 | 20 | 35.6 (5.6) | 0.81 | 123.8 (0.1) | 30.8 (0.0) | 10.1 | hard |
| 40 | | 75 | 25 | | | 7.5 (0.1) | 0.99 | 7.2 (0.0) | 34.5 (0.0) | 237.9 | hard |
| 41 | | 67.5 | 22.5 | | 10 | 4.8 (1.0) | 1.00 | 4.9 (0.0) | 32.3 (0.0) | 332.1 | hard |
| 42 | | 60 | 20 | | 20 | 3.6 (0.9) | 1.00 | 3.4 (0.0) | 30.0 (0.0) | 433.0 | hard |
| 43 | | 50 | 50 | | | 8.3 (0.5) | 0.99 | 6.6 (0.0) | 34.6 (0.0) | 259.6 | hard |
| 44 | | 45 | 45 | | 10 | 4.9 (0.6) | 1.00 | 4.4 (0.0) | 32.0 (0.0) | 363.8 | hard |
| 45 | | 40 | 40 | | 20 | 4.1 (0.9) | 1.00 | 3.5 (0.0) | 30.0 (0.0) | 429.9 | rubbery |
| 46 | | 25 | 75 | | | 9.1 (0.9) | 0.99 | 6.1 (0.0) | 34.6 (0.0) | 277.6 | hard |
| 47 | | 22.5 | 67.5 | | 10 | 7.1 (0.7) | 0.99 | 4.2 (0.0) | 32.2 (0.0) | 382.4 | hard |
| 48 | | 20 | 60 | | 20 | 4.1 (0.2) | 1.00 | 3.3 (0.0) | 30.0 (0.0) | 456.5 | pliant |
| 49 | | 25 | | 75 | | 33.3 (1.2) | 0.84 | 603.3 (2.0) | 34.9 (0.0) | 2.4 | hard |
| 50 | | 22.5 | | 67.5 | 10 | 28.5 (1.1) | 0.88 | 83.4 (0.4) | 33.6 (0.0) | 17.7 | hard |
| 51 | | 20 | | 60 | 20 | 19.8 (0.7) | 0.94 | 29.5 (0.1) | 29.8 (0.1) | 47.5 | hard |
| 52 | | 50 | | 50 | | 27.0 (1.6) | 0.89 | 80.9 (5.9) | 35.2 (0.3) | 19.4 | hard |
| 53 | | 45 | | 45 | 10 | 11.4 (0.7) | 0.98 | 25.5 (0.1) | 32.3 (0.0) | 62.0 | hard |
| 54 | | 40 | | 40 | 20 | 6.1 (0.5) | 0.99 | 13.0 (0.0) | 29.4 (0.0) | 112.5 | hard |
| 55 | | 75 | | 25 | | 9.2 (9.2) | 0.99 | 21.4 (0.0) | 35.2 (0.0) | 81.0 | hard |
| 56 | | 67.5 | | 22.5 | 10 | 7.8 (0.5) | 1.00 | 9.3 (0.1) | 31.8 (0.0) | 171.0 | hard |
| 57 | | 60 | | 20 | 20 | 5.9 (1.2) | 0.99 | 6.9 (0.0) | 29.2 (0.0) | 211.6 | hard |
| 58 | | | 25 | 75 | | 32.3 (1.5) | 0.84 | 357.4 (0.2) | 36.5 (0.0) | 4.3 | hard |
| 59 | | | 22.5 | 67.5 | 10 | 11.7 (0.4) | 0.98 | 71.7 (0.1) | 33.2 (0.0) | 22.7 | hard |
| 60 | | | 20 | 60 | 20 | 9.0 (1.4) | 0.99 | 33.6 (0.0) | 30.6 (0.0) | 45.0 | hard |
| 61 | | | 50 | 50 | | 12.1 (1.2) | 0.98 | 52.5 (0.0) | 36.0 (0.0) | 33.5 | hard |
| 62 | | | 45 | 45 | 10 | 10.3 (1.5) | 0.98 | 20.3 (0.0) | 32.6 (0.0) | 79.1 | Hard |
| 63 | | | 40 | 40 | 20 | 4.3 (0.3) | 1.00 | 10.8 (0.0) | 30.2 (0.0) | 139.9 | Rubbery |
| 64 | | | 75 | 25 | | 11.3 (1.2) | 0.98 | 12.9 (0.0) | 35.2 (0.1) | 134.3 | Hard |
| 65 | | | 67.5 | 22.5 | 10 | 8.1 (1.0) | 0.99 | 9.1 (0.0) | 32.5 (0.0) | 177.9 | Hard |
| 66 | | | 60 | 60 | 20 | 4.4 (0.1) | 1.00 | 6.3 (0.0) | 30.4 (0.0) | 239.5 | Rubbery |

Contact angle measurements were performed to polished bovine enamel. From the labial surfaces of bovine incisors, enamel disks (approximately 5×5×3 mm$^3$) were prepared (Band Saw Extrakt 300 cl; Extrakt Apparatebau, Norderstedt, Germany), embedded in methacrylate resin (Technovit 4071; Heraeus Kulzer, Hanau, Germany), and their surfaces were ground flat and polished (Polishing Machine Phoenix Alpha; Buehler, Düsseldorf, Germany; Abrasive Paper 600, 1200, 2400, 4000; Exact Apparatebau). Until usage, the specimens were stored in distilled water. Prior to each measurement, the surfaces were dried and cleaned using 100% ethanol.

To measure the contact angles of the resins, a camera based goniometer was used (G10; Krüss, Hamburg, Germany). Droplets of the liquid resins (approximately 1 µl) were placed on the enamel surface by means of a micro syringe. After 10 seconds, an image was recorded and analyzed using drop shape analysis software (DSA 10; Krüss). For each resin, the mean contact angel of three measurements was calculated. To avoid surface contamination, each measurement was performed on a new enamel disk.

Surface tensions were measured using a ring processor tensiometer (K12; Krüss). To achieve air saturation, a cup containing ethanol was placed into the metering chamber when solvent containing mixtures were gauged. Five ml of each composite were given into a Teflon mould, and the testing ring (platinum iridium alloy, RI 12; Krüss) was positioned close to the liquid surface. Measurements were performed automatically. Depending on the variance of the measured values, the device stopped gauging automatically after 5 to 20 cycles.

Kinematical viscosities were determined using a mirco-Ubbelohde processor viscosimeter (Schott; Mainz, Germany) at 25° C. For low viscous resins, glass capillaries with a capillary constant of 0.1 $mm^2 \cdot s^{-2}$ were used. High viscous composites were tested using capillaries with a capillary constant of 10 $mm^2 \cdot s^{-2}$. Three measurements were performed automatically and means and standard deviations (SD) were assessed for each material. Dynamic viscosities were calculated by multiplying the measured values with the densities of the resins. Densities of the experimental composites were calculated from data provided by the manufacturer of the monomers.

To evaluate the hardening capacities of the experimental infiltrants, 0.5% DABE and 0.5% Camphorquinone were added. The resins were applied to standardized moulds (7×4×2 $mm^3$), and light cured at 400 $mW/cm^2$ for 60 seconds (Translux CL; Hereaus Kulzer). Subsequently, their consistencies were assessed qualitatively and graded into the categories "hard", "pliant", "rubbery", "viscous", or "liquid".
2. Results The results for the experimental infiltrants are shown in Table 1. The greatest differences between the resins were found for the viscosities (3.2-6637.0 mPa·s). Resin mixtures containing high amounts of HEMA and TEGDMA showed low viscosities and high PCs. In contrast, BisGMA and UDMA showed increased viscosities and decreased PCs. Five experimental resins containing high amounts of Bis-GMA or UDMA were too viscous to be measured with the available devices. Although high variations were found for the contact angles (3.2-54.2°), their impacts on PCs were limited as they only account to PC proportional to their cosine. The addition of ethanol decreased viscosities, surface tensions, and contact angles of all mixtures leading to increased penetration coefficients for all monomer combinations. The highest PCs were found for composites containing TEGDMA, HEMA, and 20% ethanol. Composites containing high amounts of HEMA and ethanol did not cure sufficiently, leading to rubbery or liquid materials (Table 2).

Example 4

Influence of PC on Penetration Speed

Figure 5A:
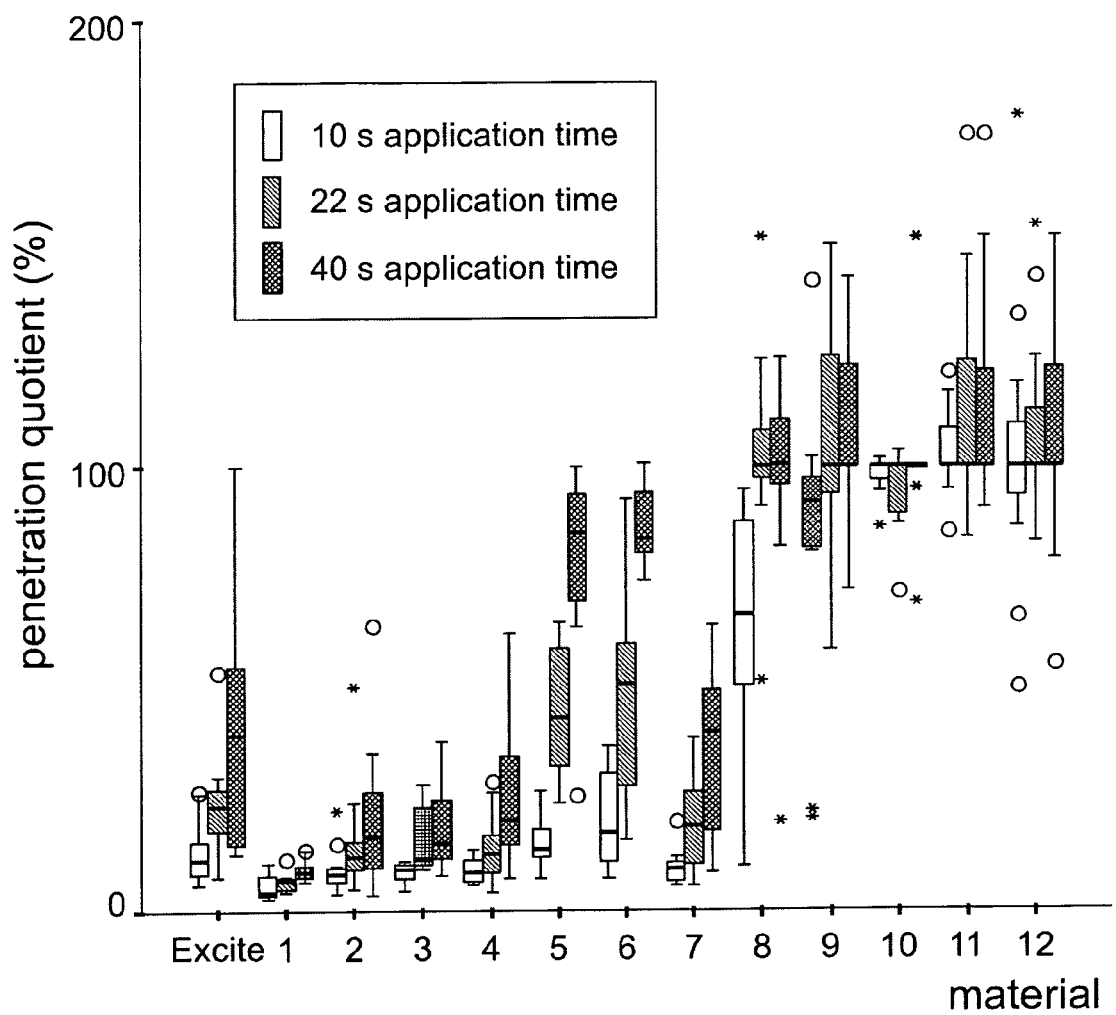
FIGS. 5A and 5B show penetration quotients (A) and absolute penetration depths (B) of the various materials (box-and-whisker plots with quartiles and medians).
Figure 5B:
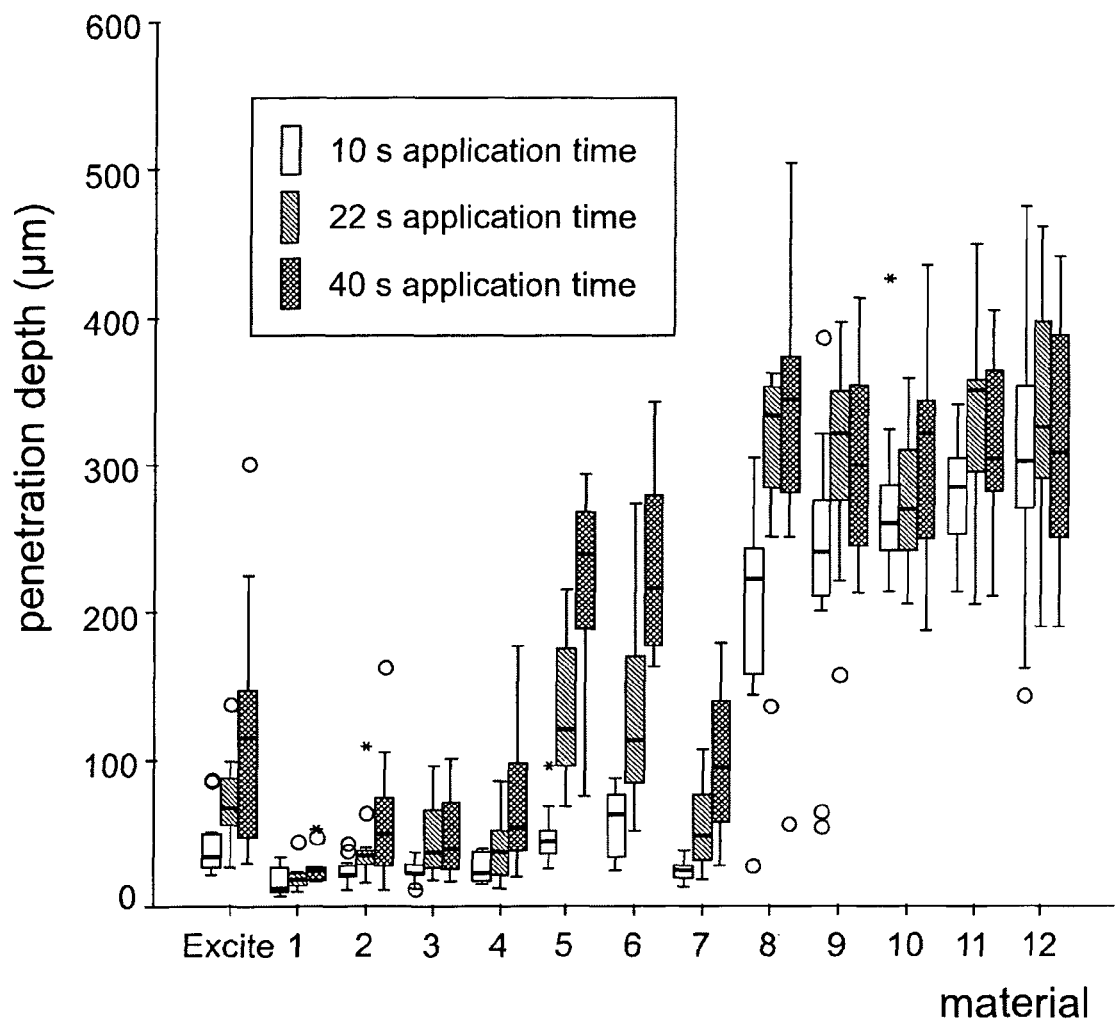

The aim of this in vitro study was to compare the penetration quotients (PQ=penetration depth/lesion depth) of twelve experimental infiltrants showing different PCs with an adhesive (Excite®; Vivadent).
1. Materials and Methods From bovine incisors, 143 specimens were prepared, embedded in epoxy resin and polished. The specimens were partially covered with nail varnish (control), and the resulting four windows were demineralised for 50 days (pH 4.95, 37° C.). After demineralisation, three of the four windows were etched with phosphoric acid (37° C.) for 5 seconds. Each of the 12 experimental materials (No 13-21 and 4-6; Table 2 as well as the adhesive were applied onto the lesions (n=11). After removing excessive material, the resins were light cured for 30 seconds. Specimens were cut perpendicularly to their surfaces and thin sections were studied using confocal microscopy (CLSM) as well as microradiography (TMR)
2. Results Mean lesion depths (SD) observed with CLSM [299 (57) µm] and TMR [296 (51) µm] were comparable. Compared to the adhesive, the PQs were significantly increased for the three infiltrants based on TEGDMA (No 4-6; Table 2 as well as for those containing BisGMA and TEGDMA (25:75) and ethanol (No 20, 21) ($p<0.05$; ANOVA). FIG. 5 shows penetration quotients (FIG. 5A) and absolute penetration depths (FIG. 5B) of the various materials.

Figure 6:
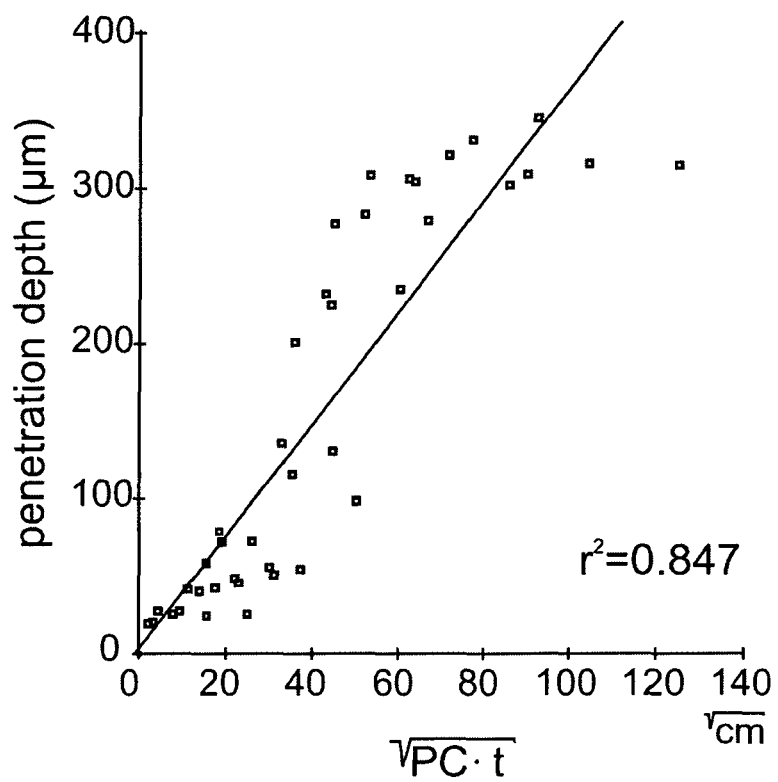
FIG. 6 shows a scatter plot of the square root of the product of penetration coefficient (PC) and time versus penetration depth.
Figure 7:
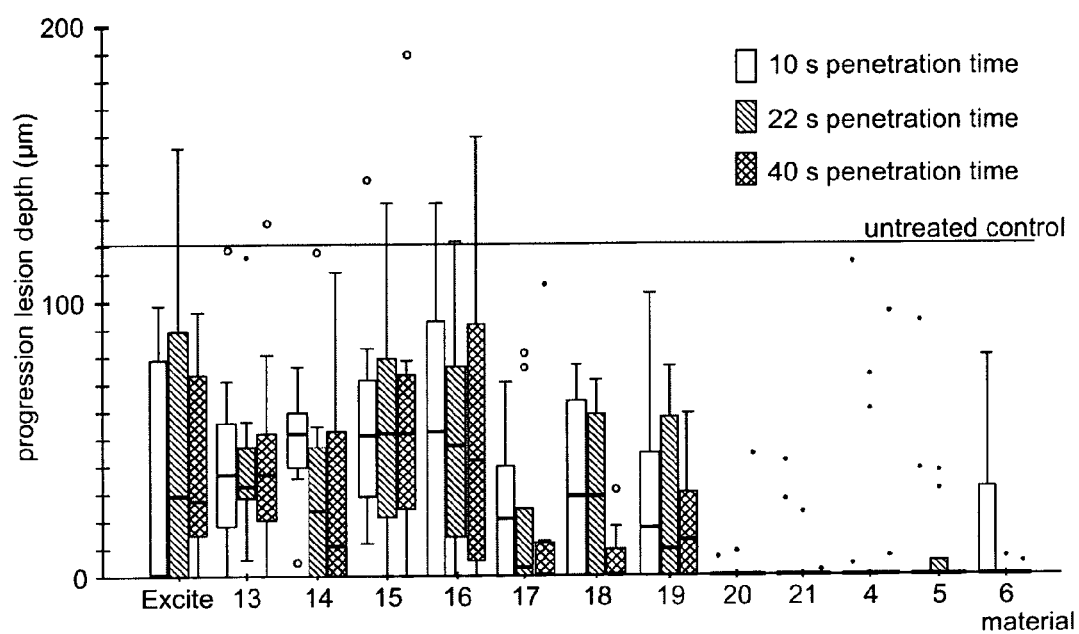
FIG. 7 shows percentage progressions of lesion depths for lesions treated with the different materials (box-and-whisker plots with quartiles and medians).

FIG. 6 shows the correlation between the penetration depth and the square root of the product of the PC and the application time ($r^2$=0.847). The good correlation indicates that the Washburn equation is capable to describe the penetration of infiltrants into enamel lesions. Therefore, the PC appears to be a suitable predictor for the ability of an infiltrant to penetrate enamel lesions rapidly. Infiltrants should have high penetration coefficients (>50 cm/s) to achieve rapid infiltration of enamel lesions.

Example 5

Figure 8:
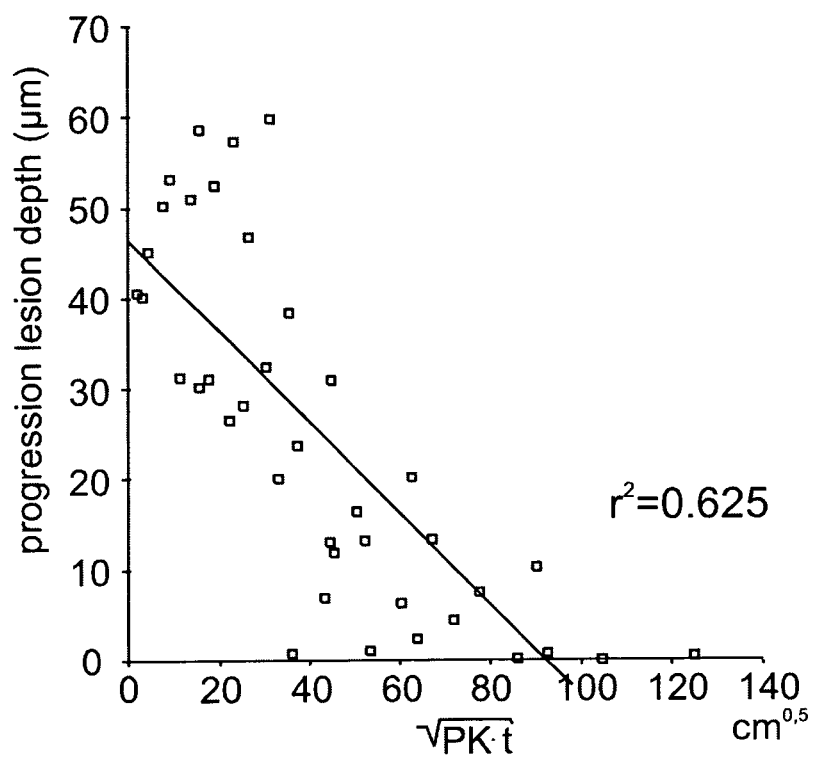
FIG. 8 shows a scatter plot of the square root of the product of penetration coefficient (PC) and time versus progression of lesion depth.

Influence of PC on Lesion Progression of Infiltrated Enamel Lesions Under Demineralising Conditions The aim of this study was to evaluate the progression of sealed artificial enamel lesions under demineralizing conditions.
1. Materials and Methods In each of 130 bovine enamel specimens, four caries like lesions were created (demineralising solution pH 4.95; 50 days). In each specimen, three lesions were etched with phosphoric acid gel for 5 seconds, whereas one lesion remained untreated. Each of 12 experimental composites (No 13-21 and 4-6; Table 2) showing different PCs as well as the adhesive Excite were applied onto the lesions (n=10). After removing excessive material, the resins were light cured for 30 seconds. Subsequently, specimens were cut perpendicular to the surface. Half of each specimen was used as baseline control. The other half was exposed to the demineralization solution for further 50 days (effect). Specimens were observed using confocal microscopy.
2. Results During the second demineralization period, mean lesion depth (SD) progressed from 299 (51) µm to 418 (76) µm (41.5%). Infiltrated lesions showed significantly reduced lesion progression compared to untreated controls ($p>0.001$;

t-test). For Excite® (PC=31.3 cm/s) as well as for infiltrants having a PC<100 cm/s, a significant progression of lesion depth could be shown (FIG. 6). Infiltrants with higher PCs showed no significant progression (p>0.05). A negative correlation between the progression of sealed lesions and the square root of the product of PC and penetration time could be found ($r^2$=0.625; p<0.01; FIG. 8). It can be concluded that infiltrants with high PCs are more suitable to inhibit lesion progression compared to those with lower PCs.

All patents, patent applications, provisional application, and publications referred to or cited herein are incorporated by reference in their entirety, including all figures and tables, to the extent they are not inconsistent with the explicit teaching of this specification.

It should be understood that the examples and embodiments described herein are for illustrative purposes only and that various modifications or changes in light thereof will be suggested to persons skilled in the art and are to be included within the spirit and purview of this application.

We claim:

1. A method of infiltrating a porous enamel lesion for treatment of a carious lesion and/or delay or prevention of further carious lesion progress in a subject in need thereof, comprising:
    (a) exposing the carious lesion to an infiltrant, which infiltrates the carious lesion;
    (b) removing surplus infiltrant; and
    (c) after said removing, curing the infiltrant, wherein the infiltrant comprises at least one low viscous light curing resin, wherein the infiltrant has a penetration coefficient of >100 cm/s, and wherein the method does not include drying the infiltrant to remove solvent, between said exposing the carious lesion to the infiltrant and said curing of the infiltrant.

2. The method according to claim 1, wherein the at least one low viscous light curing resin is selected from the group consisting of bis-GMA, 2,2-bis[4-(2-hydroxy-3-methacryloxypropoxy)phenyl]propane; bis-PMA, propoxylated bisphenol-A-dimethacrylate; bis-EMA, ethoxylated bisphenol-A-dimethacrylate; bis-MA, bisphenol-A-dimethacrylate; UDMA, 1,6-bis(methacryloxy-2-ethoxycarbonylamino)-2,4,4-trimethylhexan; UPGMA, urethane bisphenol-A-dimethacrylate; TEGDMA, triethylene glycol dimethacrylate; TEGMMA, triethylene glycol monomethacrylate; TEEGDMA, tetraethylene glycol dimethacrylate; DEGDMA, diethylene glycol dimethacrylate; EGDMA, ethylene glycol dimethacrylate; DDDMA, 1,10-decanediol dimethacrylate; HDDMA, 1,6-hexanediol dimethacrylate; PDDMA, 1,5-entanediol dimethacrylate; BDDMA, 1,4-butanediol dimethacrylate; MBDDMA ½, BDDMA-methanol-adduct ½; DBDDMA ½, BDDMA-auto-adduct ½; PRDMA, 1,2-propanediol dimethacrylate; DMTCDDA, bis(acryloxymethyl) triclodecane; BEMA, benzyl methacrylate; SIMA, 3-trimethoxysilane propylmethacrylate; SYHEMA ½, ½-cyclohexene methacrylate; TYMPTMA, trimethylolpropane trimethacrylate; MMA, methyl methacrylate; MAA, methacrylic acid; and HEMA, 2-hydroxyethyl methacrylate.

3. The method according to claim 1, wherein the infiltrant further comprises at least one additive selected from the group consisting of CQ, camphoroquinone; BL, benzil; DMBZ, dimethoxybenzoin; CEMA, N-(2-cyanoethyl)N-methylanilin; DMABEE, 4-N,N-diethylaminobenzoic acid ethyl ester; DMABBEE, 4-N,N-diethylaminobenzoic acid butyl ethoxy ester; DMABEHE, 4-N,N-diethylaminobenzoic acid 2-ethylhexyl ester; DMAEMA, N,N-diethyl aminoethyl methacrylate; DEMAEEA, N,N-(bis-ethylmetacrylate)-2-ethoxyethylamine; HMBP, 2-hydroxy-4-methoxy benzophenone; TINP, 2(2'-hydroxy-5'-methylphenyl)benzotriazol; TIN326, 2-(5-chloro-2H-benzotriazole-2-yl)-6-(1,1-dimethylethyl)-4-methyl phenol; TIN350, 2-(2H-benzotriazol-2-yl)-4-(tert-butyl)-6-(sec-butyl)phenol; Tin328, 2-(2H-benzotriazol-2-yl)-4,6-ditertpentyl phenol; HQME, hydroxyquinone monomethyl ester; BHT, 2,6-di-t-butyl-4-methyl phenol; MBP, 2,2-methylene-bis(6-t-butylphenol); MBEP, 2,2-methylenebis(6-t-butyl-4-ethylphenol); BPE, benzoic acid phenylester; MMMA, methyl methacrylate methanol adduct; CA, camphoric anhydride; HC ½, 2(3)-endo-hydroxyepicamphor; TPP, triphenyl phosphane; TPSb, triphenyl stibane; DMDDA, dimethyl dodecylamine; DMTDA, dimethyl tetradecylamine; DCHP, dicyclohexyl phthalate; DEHP, bis-(2-ethylhexyl) phthalate; and formaldehyde.

4. The method according to claim 1, wherein the subject is a human.

5. A method of infiltrating a porous enamel lesion for treatment of a carious lesion and/or delay or prevention of further carious lesion progress in a subject in need thereof, comprising:
    (a) exposing the carious lesion to an infiltrant, which infiltrates the carious lesion;
    (b) removing surplus infiltrant; and
    (c) after said removing, curing the infiltrant, wherein the infiltrant comprises at least one low viscous light curing resin comprising 22% bis-GMA, 2,2-bis[4-(2-hydroxy-3-methacryloxypropoxy)phenyl]propane; 67% TEGDMA, triethylene glycol dimethacrylate; 10% ethanol; less than 1% DABE, ethyl 4-(dimethylamino) benzoate, and less than 1% camphorquinone, and wherein the infiltrant has a penetration coefficient of >100 cm/s.

* * * * *